United States Patent
Hoss et al.

(10) Patent No.: US 7,169,600 B2
(45) Date of Patent: Jan. 30, 2007

(54) DEVICE FOR DETERMINING A GLUCOSE CONCENTRATION IN A TISSUE FLUID

(75) Inventors: Udo Hoss, Sherman Oaks, CA (US); Hans-Joerg Pfleiderer, Ulm (DE); Ralf Gessler, Baienfurt (DE); Hans-Ulrich Zieten, Illerrieden (DE); Rolf Fussgaenger, Blaustein-Weidach (DE)

(73) Assignee: Roche Diagnostics GmbH, Mannheim (DE)

( * ) Notice: Subject to any disclaimer, the term of this patent is extended or adjusted under 35 U.S.C. 154(b) by 447 days.

(21) Appl. No.: 10/782,290

(22) Filed: Feb. 19, 2004

(65) Prior Publication Data

US 2004/0191848 A1  Sep. 30, 2004

Related U.S. Application Data

(62) Division of application No. 09/620,038, filed on Jul. 20, 2000, now Pat. No. 6,852,500.

(30) Foreign Application Priority Data

Jul. 28, 1999  (DE) ................ 199 35 165

(51) Int. Cl.
*C12M 1/34*  (2006.01)
(52) U.S. Cl. ................ 435/287.1; 435/14
(58) Field of Classification Search ........... 435/14, 435/287.1; 204/409; 205/787
See application file for complete search history.

(56) References Cited

U.S. PATENT DOCUMENTS

| | | | |
|---|---|---|---|
| 5,615,671 A * | 4/1997 | Schoonen et al. | 600/322 |
| 5,640,954 A | 6/1997 | Pfeiffer et al. | 128/635 |
| 6,013,029 A | 1/2000 | Korf et al. | 600/363 |
| 6,091,976 A * | 7/2000 | Pfeiffer et al. | 600/347 |
| 6,434,409 B1 * | 8/2002 | Pfeiffer et al. | 600/347 |
| 6,591,126 B2 * | 7/2003 | Roeper et al. | 600/347 |
| 6,852,500 B1 * | 2/2005 | Hoss et al. | 435/14 |
| 6,925,393 B1 * | 8/2005 | Kalatz et al. | 702/27 |

FOREIGN PATENT DOCUMENTS

| | | | |
|---|---|---|---|
| DE | 41 30 742 A1 * | 3/1993 | |
| DE | 44 26 694 A1 * | 2/1996 | |
| DE | 44 01 400 | 6/1997 | |
| DE | WO 97/42868 * | 11/1997 | |
| WO | WO 97/42868 | 11/1997 | |

OTHER PUBLICATIONS

Dempsey et al. (1997). In vitro optimisation of a microdialysis system with potential for on-line monitoring of lactate and glucose in biological samples. Analyst 122 (185-189), pp. 185-189.

* cited by examiner

*Primary Examiner*—Ralph Gitomer
(74) *Attorney, Agent, or Firm*—Jill L. Woodburn; Sujatha Subrananiam

(57) ABSTRACT

The invention concerns an arrangement for determining the concentration of glucose in a tissue fluid. In the microdialysis technology used for this purpose, perfusate-containing glucose is transported in intermittent delivery pulses through a microdialysis probe inserted into the tissue fluid and dialysate obtained in this process is passed to a measuring cell to record the glucose content. In order to achieve an exact determination of glucose even with a reduced dialysis period, it is proposed that the starting content of glucose in the perfusate is adapted to the glucose content of the tissue fluid by means of a control device in accordance with a command variable derived from the measurement signals of the measuring cell. When the control deviation is negligible the momentary starting content of glucose in the perfusate can be determined as a measure for the glucose content of the tissue fluid.

26 Claims, 2 Drawing Sheets

DEVICE FOR DETERMINING A GLUCOSE CONCENTRATION IN A TISSUE FLUID

CROSS-REFERENCE TO RELATED APPLICATIONS

The present application is a divisional of U.S. patent application Ser. No. 09/620,038 filed on Jul. 20, 2000 now U.S. Pat. No. 6,852,500 and claims priority to German Application No. 199 35 165.1 filed Jul. 28, 1999.

FIELD OF THE INVENTION

The invention concerns a method and an arrangement for determining the concentration of glucose in a body fluid, in particular in tissue fluid with glucose-containing perfusate.

BACKGROUND AND SUMMARY OF THE INVENTION

A process and an arrangement of this type are known from WO 97/42868. This proposes intermittent delivery pulses in order to, on the one hand, enable a continuous signal calibration and, on the other hand, to accelerate the measurement process. In this process the perfusate volume which is at that moment in the microdialysis probe adjusts during the resting phases between the delivery pulses to the concentration of the tissue glucose as a result of the dialysis process whereas adjacent volume regions in the subsequent liquid column that is transported further at a high flow rate remain largely unchanged. A signal peak is observed during a delivery pulse in the measuring cell which corresponds to the concentration gradient and from which the glucose content of the dialysate and thus also of the body fluid can be determined. Perfusion fluid containing glucose, the specified glucose concentration of which defines the baseline value of the signal peak, is used for the calibration. A prerequisite for this is a linear sensor behaviour during the dialysis phases in addition to a complete concentration equilibration and it is assumed that the concentration profile in the volume transported away from the probe does not decay until it reaches the measuring cell. However, especially the latter assumption is frequently not the case since mixing occurs especially when the flow is laminar.

In addition diffusion exchange disturbs the glucose equilibrium in the tissue surrounding the probe.

Taking this as a starting point the object of the invention is to avoid the aforementioned disadvantages and in particular concentration disturbances in the body fluid and to enable an exact glucose determination with a reduced dialysis period.

The feature combinations of determining the glucose concentration in a body fluid, in particular tissue fluid, in which perfusate containing glucose is passed through a microdialysis probe inserted into the body fluid and dialysate obtained in this process is transported to a measuring cell, and in which measurement signals that correlate with the glucose content of the dialysate are measured at the measuring cell, characterized in that the starting content of glucose in the perfusate is adjusted to the glucose content of the body fluid by means of a control device in accordance with a command variable derived from the measurement signals of the measuring cell are proposed to achieve this object.

Advantageous embodiments and further developments of the invention derive from the following:

A method as described above characterized in that when the control deviation is negligible the momentary starting content of the glucose in the perfusate is determined as a measure for the glucose content of the body fluid.

A method as described in either of the preceding paragraphs characterized in that the starting content of glucose in the perfusate is determined from the adjusting variable of an adjuster of the control device.

A method as described in one of the preceding three paragraphs, characterized in that the glucose content of the perfusate is measured before it is passed into the microdialysis probe.

A method as described in one of the preceding four paragraphs, characterized in that the starting content of glucose in the perfusate is influenced by flow mixing two perfusion liquids with different glucose concentrations provided in two separate reservoirs.

A method as described in one of the preceding five paragraphs, characterized in that the perfusate is passed through the microdialysis probe (10) in alternating successive transport and dialysis intervals at different flow rates, the flow rate during the transport intervals being higher than during the dialysis intervals.

A method as described in the preceding paragraph, characterized in that the flow rate during the transport intervals is increased to such an extent that the starting content of glucose in the perfusate during passage through the microdialysis probe remains essentially constant and that during the dialysis intervals the transport is interrupted or at least the flow rate is reduced to such an extent that the glucose concentration of the dialysate approximates the glucose content of the body fluid.

A method as described in one of the preceding seven paragraphs, characterized in that the command variable is determined by integration or differentiation of the time course of the measurement signals.

A method as described in one of the preceding three paragraphs, characterized in that the command variable is determined by qualitative detection of signal peaks in the time course of the measurement signals.

A method as described in one of the preceding four paragraphs, characterized in that the command variable is determined by comparing the actual signal curve of the measurement signals with calibrated signal patterns deposited in a storage medium.

A method as described in one of the preceding five paragraphs, characterized in that the command variable is determined from the peak value of the signal time course of the measurement signals during each transport interval.

A method as described in one of the preceding six paragraphs, characterized in that the command variable can be determined according to the glucose content c of the body fluid according to the relationship $$c = \left[ \frac{S_g}{S_g \cdot (1-b) + b \cdot S_0} - 1 \right] \cdot a \cdot c_0 + c_0$$

in which $S_g$ denotes the peak value and $S_0$ denotes the base line value of the signals measured during a transport interval and $c_0$ is the momentary starting content of glucose in the perfusate and a, b are empirically determined correction factors compensating for diffusion and mixing and remaining recovery effects during the transport interval.

A method as described in one of the preceding twelve paragraphs, characterized in that the starting content of glucose in the perfusate is regulated discontinuously by a two-point control process in which the starting content of glucose in the perfusate is changed by a predetermined adjustment value when there is a control deviation.

In addition, the feature combinations of the arrangement for determining the glucose concentration in a body fluid, in particular tissue fluid, comprising a microdialysis probe for the diffusion exchange of glucose with surrounding body fluid, a perfusion device for perfusing the microdialysis probe with glucose-containing perfusate to obtain dialysate and a measuring cell located after the microdialysis probe for detecting measurement signals that correlate with the glucose content of the dialysate, characterized by a control device which adjusts the starting content of glucose in the perfusate to the glucose content of the body fluid in accordance with a command variable derived from the measurement signals of the measuring cell are proposed to achieve this object.

Advantageous embodiments and further developments of the invention derive from the following:

The arrangement as described in the preceding paragraph, characterized by an evaluation unit to determine the momentary starting content of glucose in the perfusate when the control deviation is negligible as a measure for the glucose content of the body fluid.

The arrangement as described in the preceding two paragraphs, characterized in that the perfusion device has a perfusate store and a transport unit for the preferably intermittent transport of perfusate.

The arrangement as described in the preceding paragraph, characterized in that the perfusate store has at least two separate reservoirs to hold perfusion liquids with different glucose concentrations.

The arrangement as described in the preceding two paragraphs, characterized in that the perfusate store has a first reservoir containing a glucose-free perfusion liquid and a second reservoir containing a glucose-containing perfusion liquid.

The arrangement as described in one of the preceding five paragraphs, characterized in that the control device has a flow mixer preferably comprising a mixing valve or clock-pulsed directional control valve as an adjuster to adjust the starting content of glucose in the perfusate.

The arrangement as described in the preceding paragraph, characterized in that the inlet side of the flow mixer is connected to at least two reservoirs for feeding in perfusion fluids with different glucose contents and the outlet side of the flow mixer connects a perfusate tube leading to the microdialysis probe.

The arrangement as described in one of the preceding seven paragraphs, characterized in that the control device has a digitally operated controller preferably in the form of a microcontroller.

Further, the feature combinations of arrangement for determining the glucose concentration in a body fluid, in particular tissue fluid, comprising a microdialysis probe inserted into the body fluid, at least two reservoirs for holding perfusion liquids with different glucose contents, a transport unit to perfuse the microdialysis probe with glucose-containing perfusate to obtain dialysate and a flow-through measuring cell located downstream of the microdialysis probe to register measurement signals that correlate with the glucose content of the dialysate, characterized by a control device connected on the input side to the measuring cell which control device has a flow mixer connected on the inlet side to the reservoirs and on the outlet side to the microdialysis probe which acts as an adjuster to regulate the starting content of glucose in the perfusate are proposed to achieve this object.

The idea behind the invention is to adapt the glucose content of the perfusate in a self-adjusting and adaptive manner to the glucose concentration of the body fluid. Accordingly the method proposed to achieve the above-mentioned object is to adapt the initial content of the glucose in the perfusate to the glucose content of the body fluid by means of a control unit according to a command variable derived from the measurement signals of the measuring cell. This offsets glucose gradients and hence reduces the period required for a complete dialysis equilibration. It also avoids interfering effects due to glucose gradients even with a high flow rate through the microdialysis probe and glucose variations in the body fluid.

A particularly preferred embodiment of the invention envisages determination of the momentary starting content of glucose in the perfusate as a measure for the glucose content of the body fluid when the deviation is negligible. This enables a quantitative indirect determination of the concentration by means of the momentary actual value of the regulating variable while the continuously measured signals from the measuring cell are only used as regulating input variables. Alternatively additionally, it is in principle possible to derive the glucose content of the body fluid directly from the measurement signals.

The initial content of glucose in the perfusate is advantageously determined from the adjustable variable of the adjuster of the controlling device. This measure enables the initial content to be determined accurately for example by comparison with normalized values in tables without requiring additional glucose sensors. However, in principle it is also possible to measure the glucose content of the perfusate before it is passed into the microdialysis probe.

For a variable adjustment it is advantageous when the initial content of glucose in the perfusate is influenced by flow mixing two perfusion fluids with different glucose concentrations that are kept ready in two separate reservoirs.

In a particularly preferred embodiment of the invention the perfusate is passed through the microdialysis probe in alternating consecutive transport and dialysis intervals at different flow rates, the flow rate during the transport intervals being higher than during the dialysis intervals. As a result the measurement can be shortened as a whole and the evaluation can be further simplified since an existing concentration gradient can be qualitatively detected by means of the measurement signal even if there is only a partial dialysis equilibration. The flow rate should be increased during the transport intervals to such an extent that the starting content of the glucose in the perfusate is essentially maintained as it passes through the microdialysis probe. In contrast the transport is interrupted or at least the flow rate is reduced during the dialysis intervals to such an extent that the glucose concentration in the dialysate approximates the glucose content of the body fluid.

In a particularly simple control process the command variable which defines the target value is determined by integration or differentiation of the time course of the measurement signals or by a qualitative detection of signal peaks in the time course of the measurement signals. Alternatively the command variable can be determined by comparing the actual signal time course of the measurement signals with calibrated signal patterns deposited in a storage medium. An additional method is to determine the command variable from the peak value of the signal time course of the measurement signals during each transport interval. In order to quantitatively define the regulating input signal, the command variable can be determined according to the glucose content c of the body fluid using the relationship $$c = \left[ \frac{S_g}{S_g \cdot (1-b) + b \cdot S_0} - 1 \right] \cdot a \cdot c_0 + c_0$$

in which $S_g$ denotes the peak value and $S_0$ denotes the base line value of the signals measured during a transport interval and $c_0$ is the momentary starting content of glucose in the perfusate and a, b are empirically determined correction factors compensating for diffusion and mixing and remaining recovery effects during the transport interval.

A particularly simple control function envisages that the initial content of glucose in the perfusate is adjusted discontinuously by a two-point control process in which the starting content of the glucose in the perfusate is changed by a predetermined adjusting value when there is a deviation.

With regard to a measuring arrangement, a control device is proposed to achieve the above-mentioned object which adapts the starting content of the glucose in the perfusate to the glucose content of the body fluid on the basis of a command variable derived from the measurement signals of the measuring cell. An evaluation unit is provided in a preferred embodiment which determines the glucose content of the body fluid corresponding to the momentary starting content of glucose in the perfusate when the deviation is negligible.

The perfusion device contains a store of perfusate and a transport unit to transport perfusate. The transport unit preferably operates at intervals i.e. at different delivery rates in successive time intervals. In order to vary the initial glucose content it is advantageous if the perfusate store has at least two separate reservoirs to hold perfusion liquids with different glucose concentrations. Advantageously the perfusate store has a first reservoir containing a glucose-free perfusion liquid and a second reservoir containing a glucose-containing perfusion liquid. In this case the glucose content in the latter should be above the physiological thresholds. A controller for adjusting the starting content of the glucose in the perfusate which is simple to construct is preferably provided by a flow mixer composed of a mixing valve or a clock-pulsed directional control valve as the adjuster. In this case it is advantageous for the flow mixer to be connected on the inlet side with at least two reservoirs to supply perfusion fluids with different glucose contents and to discharge into a perfusate tube leading to the microdialysis probe.

The control device advantageously has a controller that operates digitally preferably by means of a micro-controller in order to process the signal flow in a variable manner.

BRIEF DESCRIPTION OF THE DRAWINGS

The invention is elucidated in more detail in the following on the basis of an embodiment example shown schematically in the drawing.

DETAILED DESCRIPTION OF THE DRAWINGS

Figure 1:
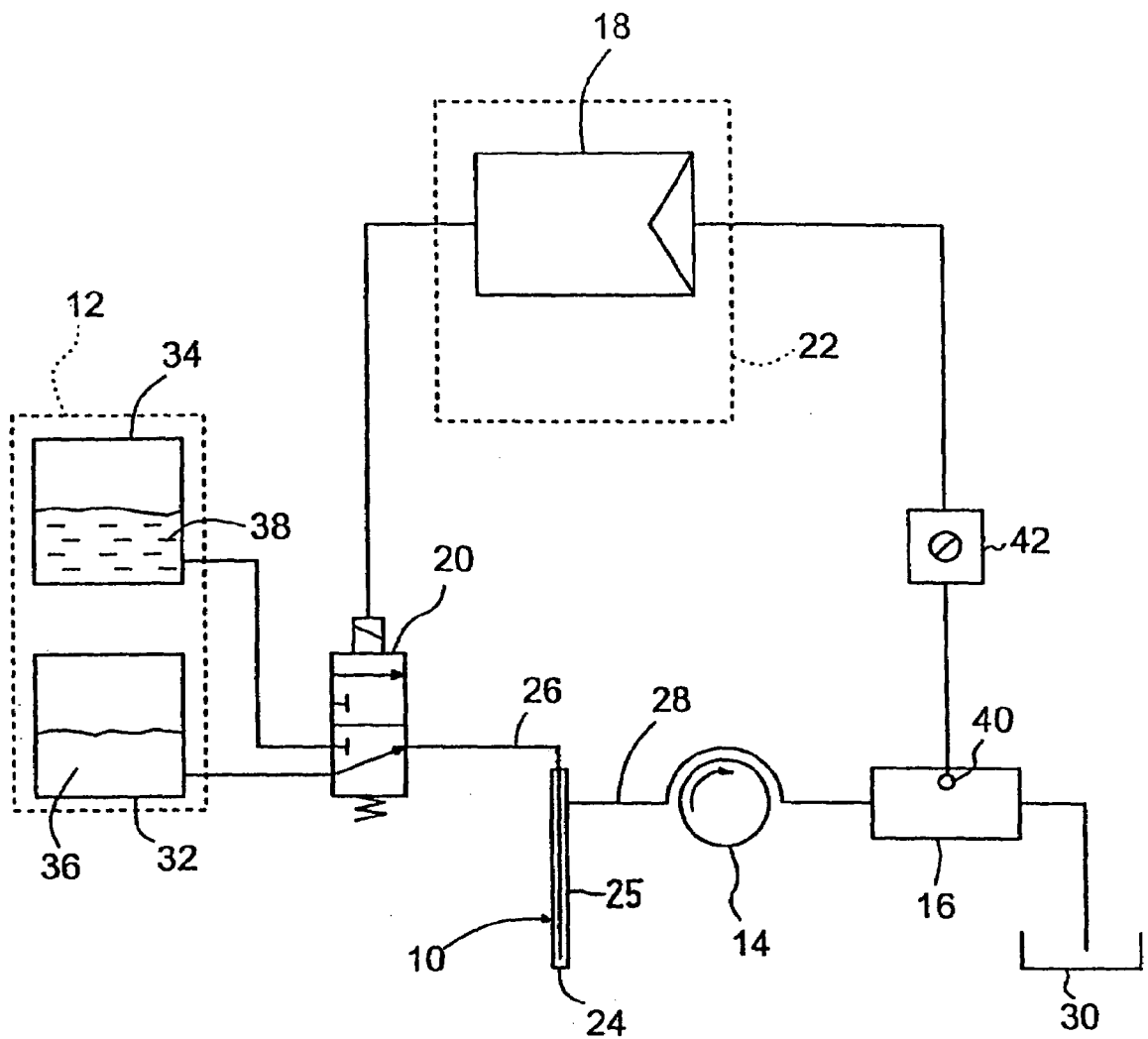
FIG. 1 shows a block diagram of a microdialysis arrangement for determining the concentration of glucose in a tissue fluid and FIG. 2 shows a time-dependency diagram of the perfusate flow, the measured glucose signal in the dialysate and the adaptively readjusted glucose concentration in the perfusate.

The microdialysis arrangement shown in the figure is essentially composed of a microdialysis probe 10 that can be implanted in the subcutaneous tissue of a test person, a perfusion device 12, 14 for the intermittent perfusion of the microdialysis probe 10 with glucose-containing perfusate, a flow-through measuring cell 16 to detect the glucose content in the dialysate that flows through, a control device 18, 20 to adjust the starting content of the glucose in the perfusate to the glucose content of the tissue fluid and an evaluation unit 22 to determine the glucose content of the tissue fluid.

The microdialysis probe 10 has a dialysis membrane 24 which enables a diffusion exchange of glucose between the perfusate located in the probe and the interstitial liquid surrounding the probe while obtaining dialysate. For this purpose a flow-through channel is provided in the tube-shaped double bore probe housing 25 which is at least partially bordered by the dialysis membrane 24 and which in the proximal probe region is connected on the inlet side with a perfusate tube 26 to pass in perfusate and on the outlet side with a dialysate tube 28 to discharge the dialysate formed from the perfusate during the dialysis process. The dialysate can be further transported via the dialysate tube 28 to the measuring cell 16 and from there into a collecting vessel 30. Suitable microdialysis probes of the described type are well-known especially from DE-A 33 42 170 or U.S. Pat. No. 4,694,832 and can be obtained from the CMA/Microdialysis AB company located in Solna, Sweden under the name "CMA 60 Microdialysis Catheter" or "CMA 70 Brain Microdialysis Catheter".

In order to supply the microdialysis probe 10 at intervals with perfusate containing glucose, the perfusion device contains a store of perfusate 12 and a transport unit 14. The perfusate store 12 is composed of two separate reservoirs 32, 34 one of which contains a glucose-free perfusion liquid 36 and the other contains a perfusion liquid 38 to which glucose has been added at a specified concentration. The glucose concentration of the liquid 38 is expediently more than 4 g/l in order that the physiological range of tissue glucose can be covered in the perfusate by mixing the liquids 36 and 38 in the manner described below. A peristaltic pump 14 operated at intervals is provided as a feeding unit to transport the perfusate in metered delivery pulses of a few microliters through the microdialysis probe 10 and the subsequent measuring cell 16. It is preferably located in the dialysate tube 28 in order during the transport pauses to isolate the microdialysis probe 10 from the measuring cell 16 arranged extracorporeally.

The measuring cell 16 through which perfusion fluid and the dialysate contained therein flows, has an electrode sensor 40 which operates electrochemically-enzymatically for continuous signal acquisition. The sensor 40 has a measuring electrode that is not shown which is supplied with the dialysate that serves as the electrolyte and is used to continuously register as a continuous measuring current, the measurement signals that are linearly dependent on the glucose content of the dialysate. Further details of this measuring principle are known in the prior art in particular from DE-A 44 01 400 to which special reference is herewith made. Obviously the measurement signals also reflect the glucose content of the body fluid insofar as a complete equilibration of the concentration gradient between the perfusate and the body fluid has taken place in the microdialysis probe or the degree of equilibration is known.

The signals measured by the sensor 40 are electronically processed in the subsequent measurement transducer 42 and fed into a digital controller 18 of the controlling device as a chronological sequence of digital values by means of a clock-pulsed analogue-digital converter. In this case the controller 18 is a microcontroller which also forms the evaluation unit 22. The output side of the controller 18 is connected to a directional control valve 20 as an adjuster of the control unit for adjusting the initial content of glucose in the perfusate. In a spring-centred first switch position the directional control valve 20 connects the perfusate tube 26 to the glucose-free reservoir 32 and, in a second electromagnetically actuated switch position, to the glucose-containing reservoir 34. Hence, the glucose concentration in the perfusate can be influenced as a regulated variable in a synchronized operation by suitable selection of the switching frequency, by the quantity ratio of the liquids 36, 38 sucked in by the peristaltic pump 14 and by the flow mixing which occurs subsequently in the perfusate tube 26.

Figure 2:
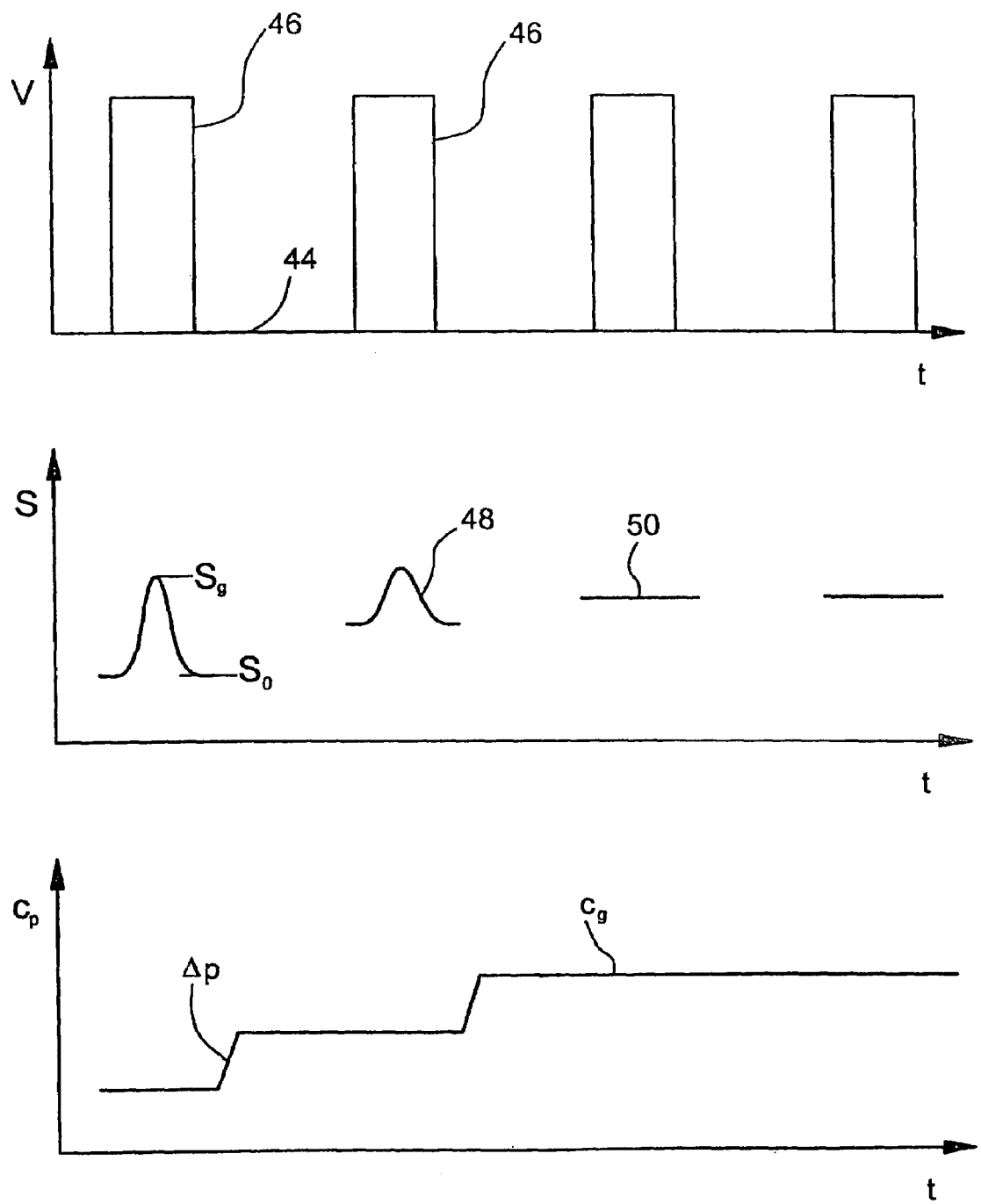

When the microdialysis arrangement is in operation according to the above-mentioned diagram in FIG. 2, the perfusate is pumped in transport intervals 46 separated by resting and dialysis intervals 44 through the microdialysis probe 10 and the measuring cell 16. The dialysis intervals can be dimensioned such that the glucose content of the perfusate volume resting in the microdialysis probe 10 is almost completely adjusted to the tissue glucose by diffusion exchange. In contrast the glucose concentration in the perfusate remains essentially unchanged during the transport intervals 46 due to rapid passage through the probe. The degree of equilibration or the recovery depends among others on the residence time and the flow rate of the perfusate in the microdialysis probe 10. In the embodiment example shown in FIG. 2 the duration of the dialysis interval is 360 sec when transport is interrupted whereas the duration of a transport interval is 180 sec at a flow rate V of 0.08 µl/s.

With each delivery pulse the dialysate formed in the previous dialysis interval is displaced completely in a transport or liquid column from the microdialysis probe 10 at least into the dialysis tube 28 and preferably up to the measuring cell 16. Accordingly a signal S is registered there during the transport intervals 46 which, when there are differences in concentration between the tissue and perfusate glucose, displays a corresponding peak or extreme value $S_g$ and a base line value $S_0$ which corresponds to the starting concentration of glucose in the perfusate (middle diagram in FIG. 2).

In order to adjust the starting glucose in the perfusate to the tissue glucose, a command variable which corresponds to the tissue glucose is derived from the measurement signals by means of the evaluation unit 22 and fed into the controller 18 to generate the deviation from the controlled variable i.e. the momentary value for the starting glucose. In this case the command variable correlates with the signal peaks $S_g$ whereas the control variable can be acquired from the base line value $S_0$.

For a particularly simple control it is sufficient that the command variable or the control difference is determined by a qualitative detection of signal peaks $S_g$ and the starting content of glucose in the perfusate is discontinuously adapted by a two-point control process. In this process the initial glucose content $c_p$ is increased by a predetermined value Δp when there is a positive peak (signal peak 48) using the adjuster 20 and is correspondingly reduced when there is a negative peak (signal dip; not shown). A slight equilibration or recovery (<50%) during the dialysis intervals is already sufficient for this controlled operation and hence its duration can be correspondingly reduced.

The adjusting signal can only be converted in the case of constant transport intervals after a dialysis interval is completed. In order to avoid this dead time, it is also conceivable that the duration of the momentary transport interval could be extended when there is a deviation to ensure that the perfusion liquid containing the re-adjusted glucose content can immediately pass into the microdialysis probe 10.

When the deviation is negligible, a constant signal 50 is finally observed which indicates that the initial glucose content $c_p$ agrees with the actual value $c_g$ of the tissue glucose (FIG. 3 below). Hence an error-prone direct evaluation of the measurement signals is not necessary and the method enables the tissue glucose to be determined indirectly from the equilibrium values $c_p$ when a constant signal 50 occurs. This can be accomplished without additional measurements by the fact that the initial content of the glucose in the perfusate is determined by means of the evaluation unit 22 from the actual adjustable variable i.e. the switching frequency of the valve 20, optionally by comparison with assigned calibration values.

One method for the quantitative evaluation of the measurement signals is to determine the command variable by pattern recognition i.e. by comparing the actual signal curve of the measurement signals with calibrated signal patterns that are deposited in a storage medium. Alternatively the deviation can be determined as a difference between the peak value and the base line value of the signal curve of the measurement signals. Hence in this case the actual values of the control variable are recorded by measurement as the base line value $S_0$.

As outlined above, the sensor signal is evaluated only during the high flow phase. This signal consists of the part $S_g$ belonging to the dialysis phase and being proportional to the tissue glucose concentration and the signal $S_0$ belonging to the high flow rate representing almost the initial perfusate glucose concentration. In order to achieve a control which is independent of variations in sensitivity, the command variable can be determined according to the glucose content c of the tissue liquid using the relationship $$c = \frac{S_g}{S_0} * c_0$$

in which $c_0$ is the momentary starting glucose content in the perfusate which can be determined by the adjustable variable.

In order to take into account further influence parameters, the tissue glucose concentration may be calculated as follows:

$$c = \left[\frac{S_g}{S_g \cdot (1-b) + b \cdot S_0} - 1\right] \cdot a \cdot c_0 + c_0$$

where a and b are empirically determined correction factors compensating for diffusion and mixing and remaining recovery effects during the transport interval. The peak value $S_g$ is the sensor value at a definite time point during the transport interval. This time point may be determined in vitro and is given by the time it takes to push the dialysate from the microdialysis probe to the glucose sensing unit, i.e. the measuring cell 16. $S_0$ may be obtained as the mean value of the sensor values 60 seconds before and after the time point of $S_g$.

It is conceivable that the previously described principle of self-adapting control of the glucose content can also be used in the case of measurements with a continuous perfusate flow. In principle this microdialysis technique is not restricted to subcutaneous measurements on the human body. Rather it is possible to examine other body fluids such as blood and optionally ex vivo.

What is claimed is:

1. A device for determining a glucose concentration in a tissue fluid, the device comprising
    a microdialysis probe for a diffusion exchange of glucose with surrounding tissue fluid,
    a perfusion device for perfusing the microdialysis probe with glucose-containing perfusate to obtain dialysate,
    a dialysate glucose content measuring cell located downstream of the microdialysis probe, and
    a control device, which adjusts the content of glucose in the perfusate upstream of the microdialysis probe to the glucose content of the tissue fluid in accordance with a command variable derived from measurement signals of the measuring cell.

2. The device of claim 1 further comprising an evaluation unit to determine a momentary starting content of glucose in the perfusate when a control deviation is negligible as a measure for the glucose content of the tissue fluid.

3. The device of claim 2 wherein the perfusion device has a perfusate store and a transport unit for an intermittent transport of perfusate.

4. The device of claim 2 wherein the control device has a flow mixer that includes a valve formed to adjust the starting content of the glucose in the perfusate.

5. The device of claim 2 wherein the control device has a digital controller.

6. The device of claim 1 wherein the perfusion device has a perfusate store and a transport unit for an intermittent transport of perfusate.

7. The device of claim 6 wherein the perfusate store has at least two separate reservoirs to hold perfusion liquids with different glucose concentrations.

8. The device of claim 6 wherein the perfusate store has a first reservoir containing a glucose-free perfusion liquid and a second reservoir containing a glucose-containing perfusion liquid.

9. The device of claim 6 wherein the control device has a flow mixer that includes a valve formed to adjust a starting content of the glucose in the perfusate.

10. The device of claim 9 wherein the control device has a digital controller.

11. The device of claim 1 wherein the control device has a flow mixer that includes a valve formed to adjust a starting content of the glucose in the perfusate.

12. The device of claim 11 wherein the valve is a mixing valve or a clock-pulsed directional control valve.

13. The device of claim 11 wherein the flow mixer includes an inlet side connected to reservoirs for feeding in perfusion fluids with different glucose concentrations and an outlet side connected to a perfusate tube leading to the microdialysis probe.

14. The device of claim 11 wherein the control device has a digital controller.

15. The device of claim 1 wherein the control device has a digital controller.

16. The device of claim 15 wherein the controller is a microcontroller.

17. A device for determining a glucose concentration in a tissue fluid, comprising
    a microdialysis probe inserted into the tissue fluid,
    at least two reservoirs for holding perfusion liquids with different glucose concentrations,
    a transport unit to perfuse the microdialysis probe with glucose-containing perfusate to obtain dialysate,
    a flow-through measuring cell located downstream of the microdialysis probe to register measurement signals that correlate with the glucose content of the dialysate, and
    a control device connected on an input side to the measuring cell, which control device has a flow mixer connected on an inlet side to the reservoirs and on an outlet side to the microdialysis probe, which acts as an adjuster to regulate the content of glucose in the perfusate upstream of the microdialysis probe.

18. A device for determining the glucose concentration in a tissue fluid, comprising
    a microdialysis probe,
    a perfusion device in communication with the micro dialysis probe to perfuse the microdialysis probe with glucose-containing perfusate to obtain dialysate,
    a measuring cell being located downstream of the microdialysis probe, and having an electrode sensor formed to detect measurement signals that correlate with the glucose content of the dialysate, and
    a control device, which adjusts the content of glucose in the perfusate upstream of the microdialysis probe to the glucose content of the tissue fluid in accordance with a command variable corresponding with the glucose concentration of the tissue fluid and being derived from the measurement signals of measuring cell.

19. The device of claim 18 further comprising an evaluation unit to determine a momentary starting content of glucose in the perfusate.

20. The device of claim 18 wherein the perfusion device has a perfusate store and a transport unit.

21. The device of claim 20 wherein the perfusate store has at least two separate reservoirs to hold perfusion liquids with different glucose concentrations.

22. The device of claim 20 wherein the perfusate store has a first reservoir containing a glucose-free perfusion liquid and a second reservoir containing a glucose-containing perfusion liquid.

23. The device of claim 18 wherein the control device has a flow mixer comprising a mixing valve or clock-pulsed directional control valve as an adjuster formed to adjust starting content of glucose in the perfusate.

24. The device of claim 23 wherein an inlet side of the flow mixer is connected to at least two reservoirs for feeding in perfusion fluids with different glucose concentrations and an outlet side of the flow mixer connects a perfusate tube leading to the microdialysis probe.

25. The device of claim 18 wherein the control device has a digital controller.

26. A device for determining a glucose concentration in a tissue fluid, comprising
    a microdialysis probe inserted into the tissue fluid,
    at least two reservoirs for holding perfusion liquids with different glucose concentrations,
    a transport unit in communication with the microdialysis probe and the at least two reservoirs, to perfuse the microdialysis probe with glucose-containing perfusate to obtain dialysate,
    a flow-through measuring cell located downstream of the microdialysis probe and formed to register measurement signals that correlate with the glucose content of the dialysate, and a control device in communication wit the measuring cell, the control device having a flow mixer in communication with at least two reservoirs and with the microdialysis probe to act as an adjuster to regulate the content of glucose in the perfusate upstream of the microdialysis probe.

* * * * *